(12) United States Patent
Mirelez, Jr. et al.

(10) Patent No.: US 11,786,344 B2
(45) Date of Patent: Oct. 17, 2023

(54) SYSTEM AND METHOD OF DIGITAL WORKFLOW FOR SURGICAL AND RESTORATIVE DENTISTRY

(71) Applicant: InstaRisa Digital Dental Technologies, LLC, Tallahassee, FL (US)

(72) Inventors: Jose Arthur Mirelez, Jr., Clovis, CA (US); Jeffrey Bynum, Winter Haven, FL (US); Fernando Polanco, Clovis, CA (US); Chandeep Singh Purewal, Las Vegas, NV (US)

(73) Assignee: InstaRisa Digital Dental Technologies, LLC, Tallahassee, FL (US)

( * ) Notice: Subject to any disclaimer, the term of this patent is extended or adjusted under 35 U.S.C. 154(b) by 0 days.

(21) Appl. No.: 17/532,996

(22) Filed: Nov. 22, 2021

(65) Prior Publication Data

US 2022/0160478 A1    May 26, 2022

Related U.S. Application Data

(60) Provisional application No. 63/117,283, filed on Nov. 23, 2020.

(51) Int. Cl.
| | |
|---|---|
| *A61C 13/00* | (2006.01) |
| *G16H 10/60* | (2018.01) |
| *G16H 30/20* | (2018.01) |
| *A61C 8/00* | (2006.01) |
| *A61C 9/00* | (2006.01) |
| *A61C 19/04* | (2006.01) |

(52) U.S. Cl.
CPC .......... *A61C 13/0004* (2013.01); *A61C 8/005* (2013.01); *A61C 8/008* (2013.01); *A61C 8/0095* (2013.01); *A61C 9/0006* (2013.01); *A61C 9/0053* (2013.01); *A61C 19/04* (2013.01); *G16H 10/60* (2018.01); *G16H 30/20* (2018.01)

(58) Field of Classification Search
CPC ... A61C 8/0001; A61C 8/008; A61C 13/0004; A61C 13/00; A61C 13/34; G16H 10/60; G16H 30/20
See application file for complete search history.

(56) References Cited

U.S. PATENT DOCUMENTS

| | | | |
|---|---|---|---|
| 2012/0088208 A1 | 4/2012 | Schulter et al. | |
| 2012/0295223 A1 | 11/2012 | Robb et al. | |
| 2014/0011160 A1* | 1/2014 | Jorneus | A61C 8/0066 433/173 |
| 2015/0327958 A1 | 11/2015 | Llop et al. | |

(Continued)

FOREIGN PATENT DOCUMENTS

| | | |
|---|---|---|
| EP | 3 123 975 A1 | 2/2017 |
| EP | 3 415 113 A2 | 12/2018 |

(Continued)

*Primary Examiner* — Amy R Sipp
*Assistant Examiner* — Sydney J Pulvidente
(74) *Attorney, Agent, or Firm* — SEED INTELLECTUAL PROPERTY LAW GROUP LLP

(57) ABSTRACT

A digital workflow process and associated devices and tools for providing dental restorations and, more particularly, to precise and efficient reconstruction and replacement of teeth using novel digital workflows and improved dental scan bodies, abutments and other dental devices and tools to efficiently achieve a more precise fit and optimal form and function.

11 Claims, 20 Drawing Sheets

(56) References Cited

U.S. PATENT DOCUMENTS

| | | |
|---|---|---|
| 2016/0235505 A1 | 8/2016 | Selberis et al. |
| 2017/0027667 A1 | 2/2017 | Thomé et al. |
| 2018/0325631 A1* | 11/2018 | Christiansen ........ A61C 8/0001 |
| 2019/0298501 A1 | 10/2019 | Chiou et al. |
| 2019/0374317 A1 | 12/2019 | Chiou et al. |
| 2020/0146783 A1 | 5/2020 | Philibin |
| 2020/0146784 A1 | 5/2020 | Philibin |
| 2020/0146785 A1 | 5/2020 | Philibin |
| 2020/0360118 A1 | 11/2020 | Olivier et al. |

FOREIGN PATENT DOCUMENTS

| | | |
|---|---|---|
| WO | 2016/110855 A1 | 7/2016 |
| WO | 2017/085288 A1 | 5/2017 |
| WO | 2019/043633 A1 | 3/2019 |
| WO | 2020/162730 A1 | 8/2020 |
| WO | 2020/183115 A1 | 9/2020 |

\* cited by examiner

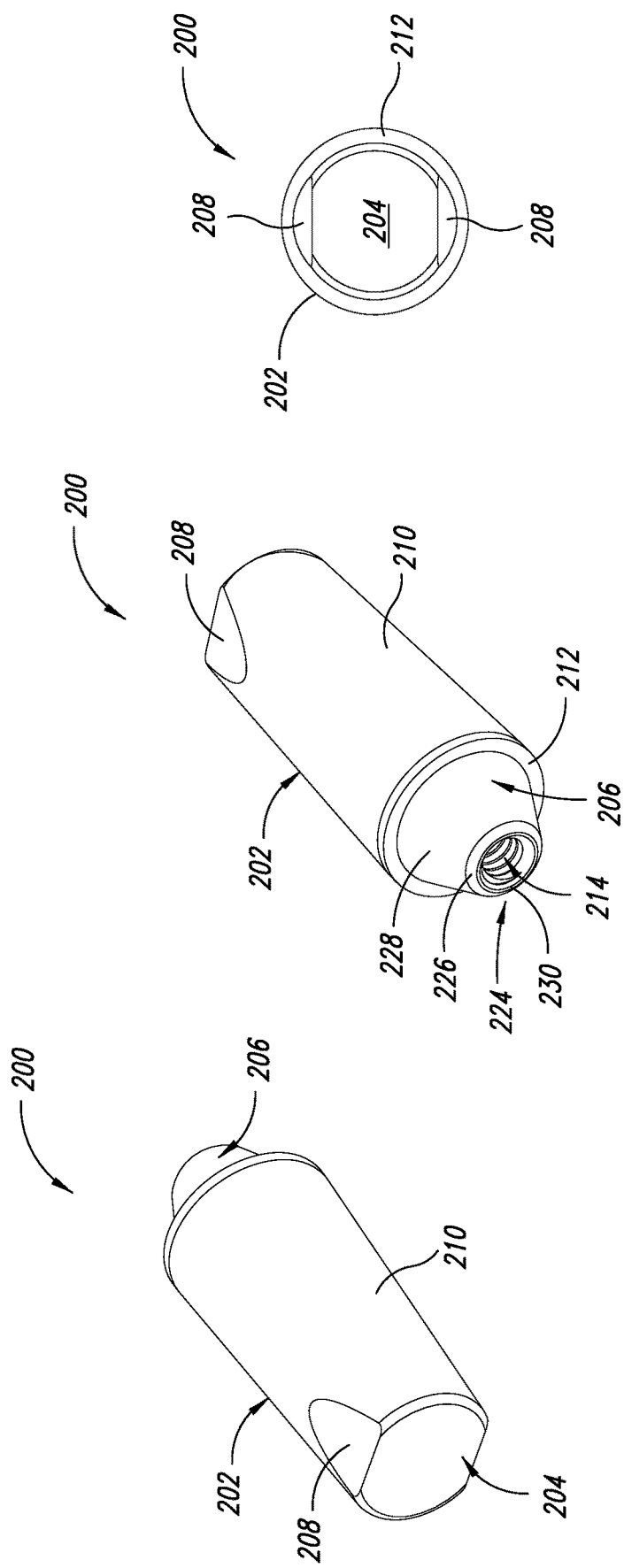

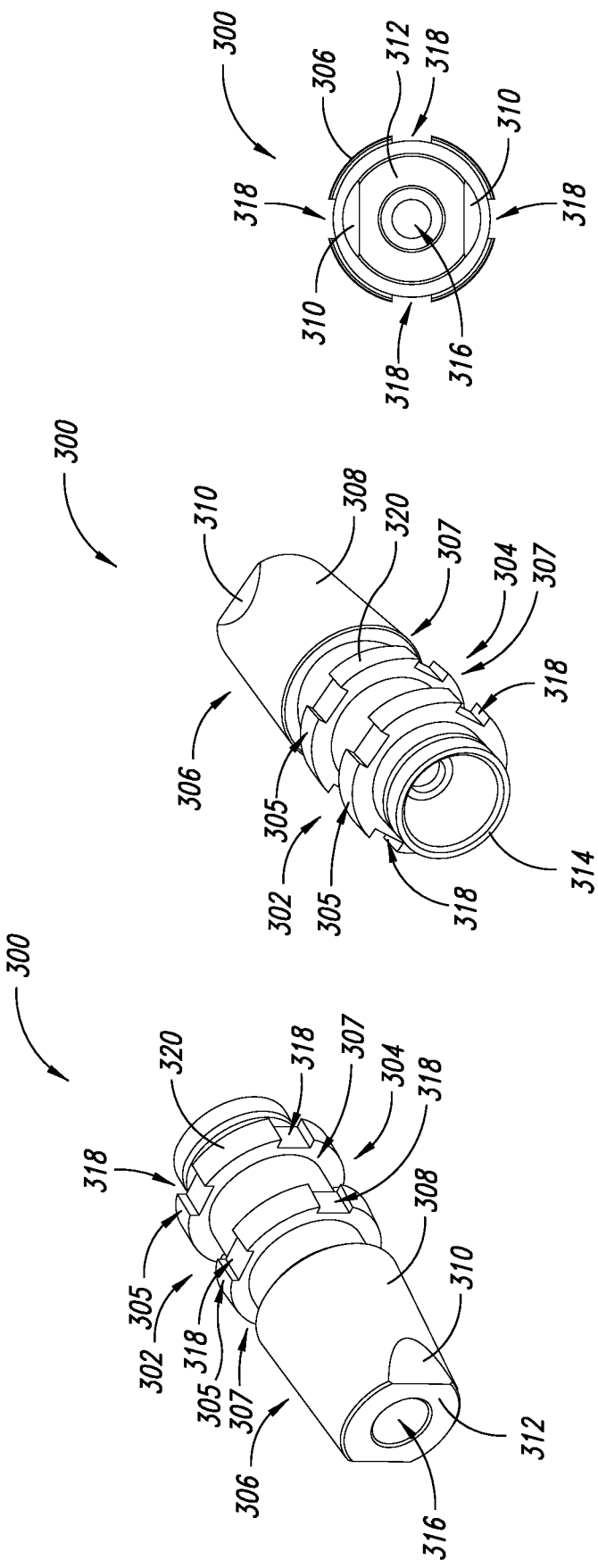

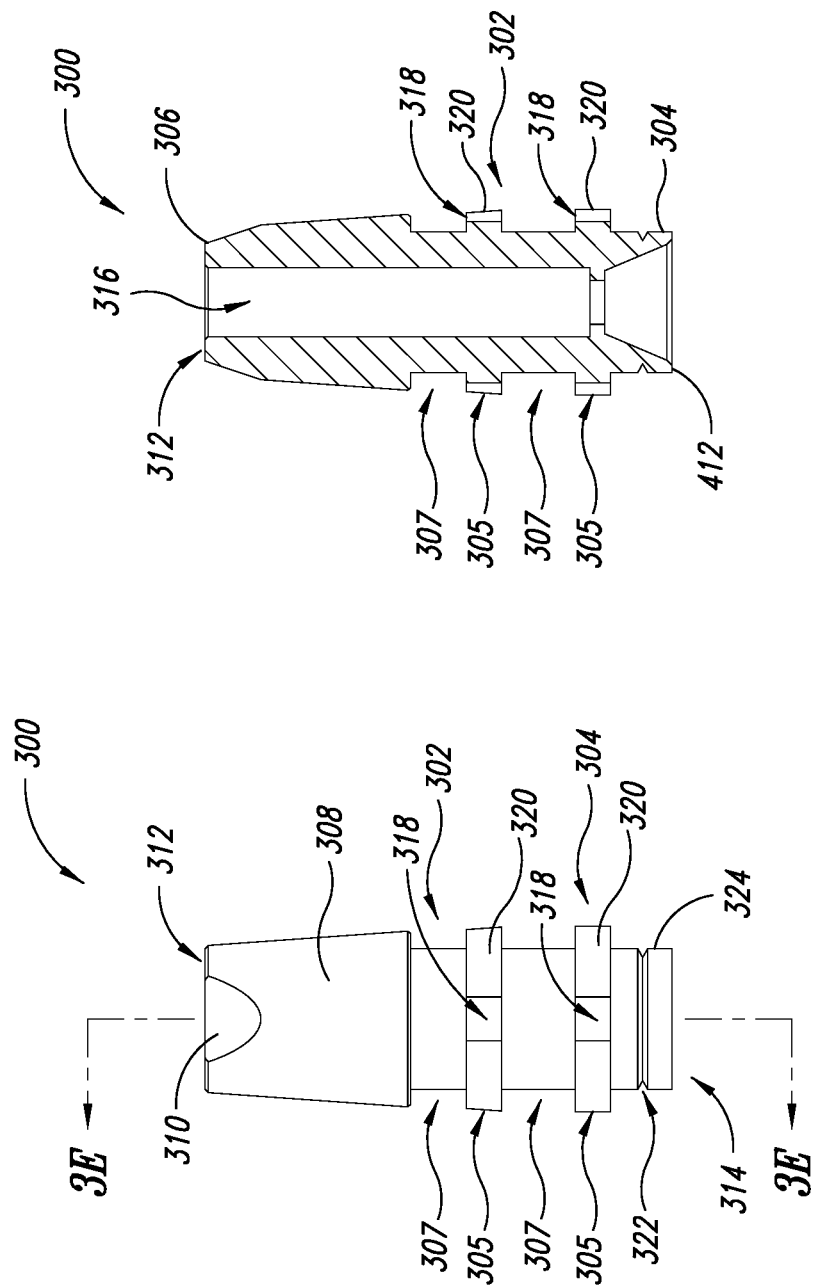

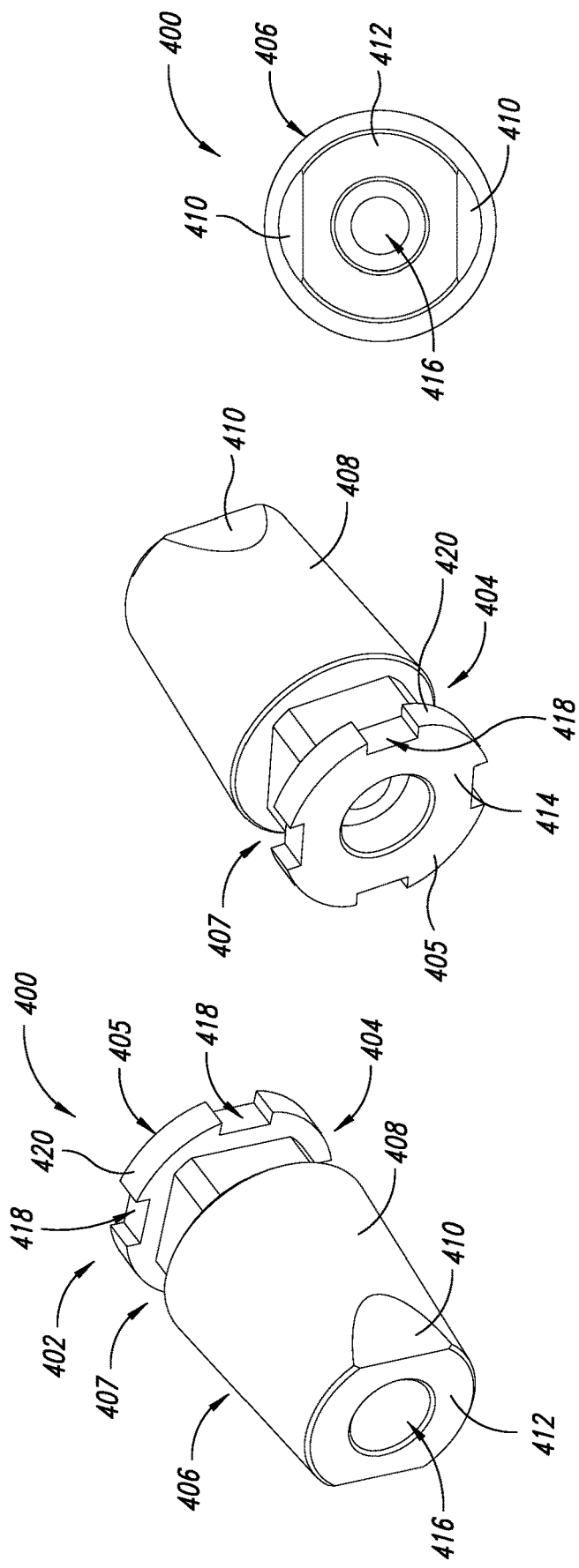

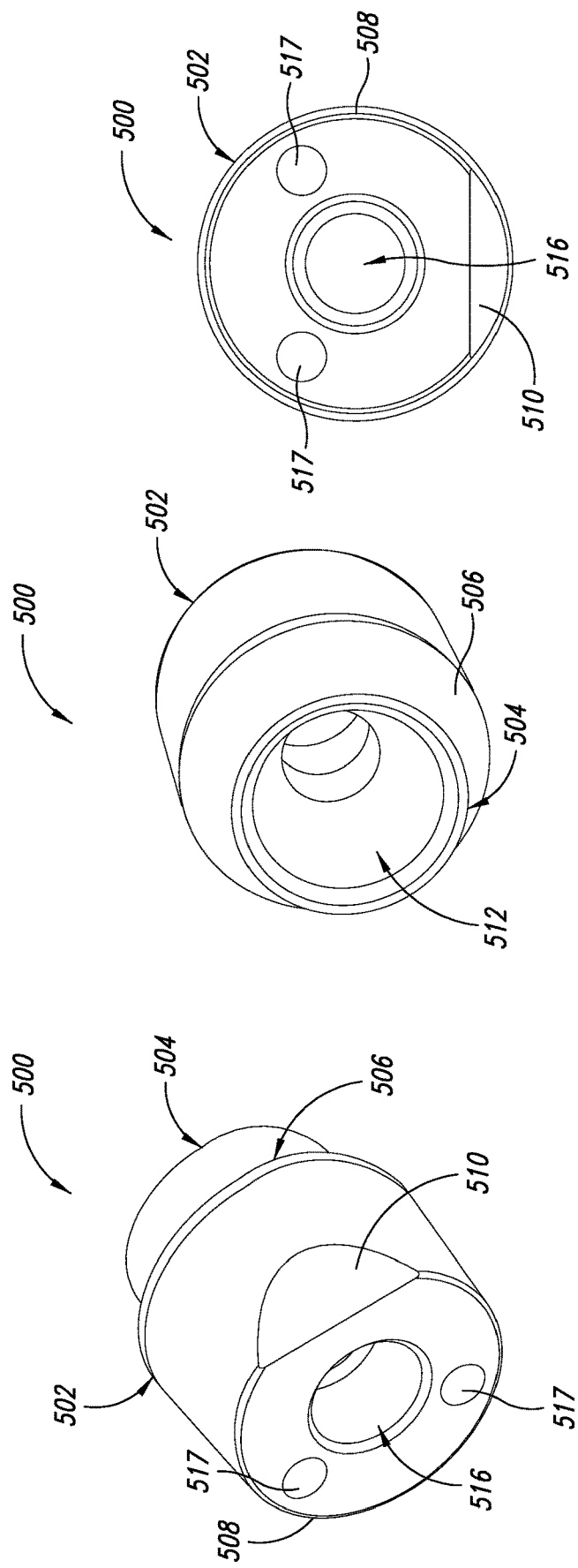

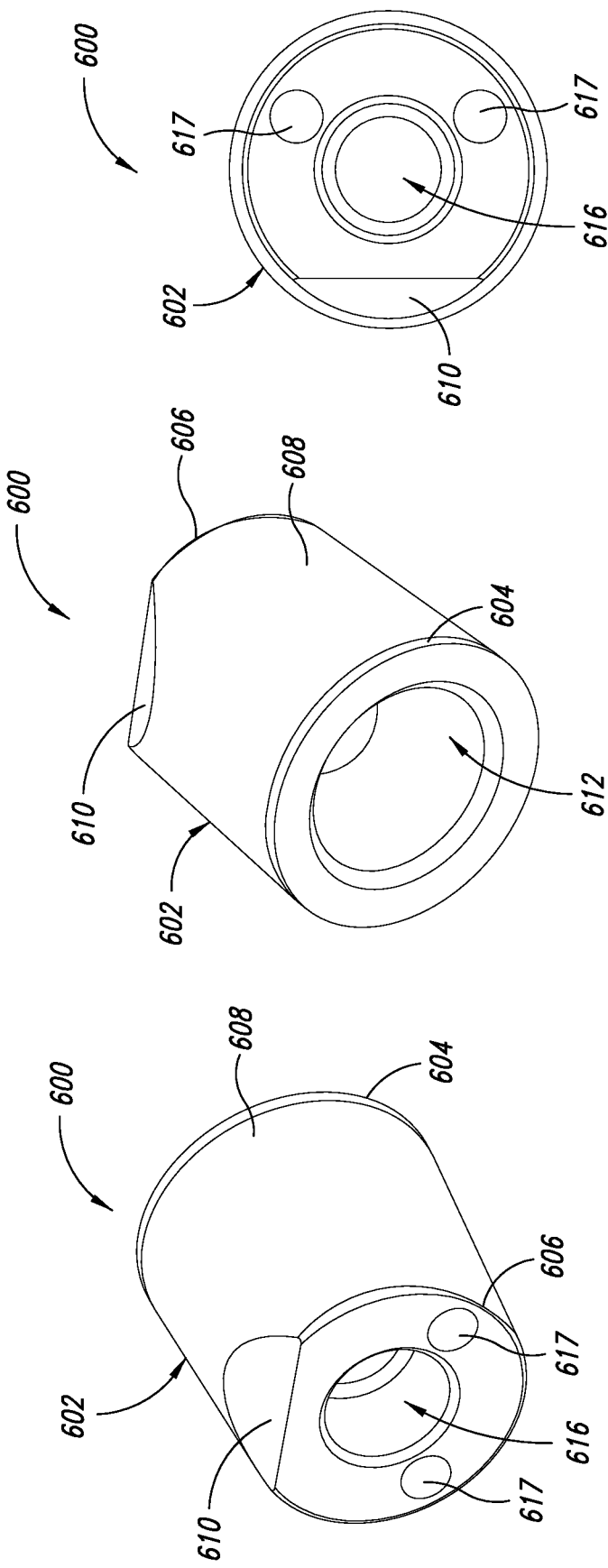

SYSTEM AND METHOD OF DIGITAL WORKFLOW FOR SURGICAL AND RESTORATIVE DENTISTRY

BACKGROUND

Technical Field

The present disclosure is directed to the process and tools used for dental restorations and, more particularly, to precise and efficient reconstruction and replacement of teeth using novel digital workflows and improved dental scan bodies, abutments and other dental devices and tools that provide a more precise fit and optimal form and function.

Description of the Related Art

Restoring the dentition of an edentulous patient or a patient with a failing dentition has traditionally been a laborious and difficult task for surgical and restorative dentists. Analog techniques require a significant amount of time and multiple appointments to provide functional and esthetic results for the patient. Diagnosis and treatment planning are limited to either the times the patient is physically in the presence of the diagnosing doctor or to the use of two-dimensional photography that limits the data available to only what was captured in a static position.

Multiple try-in and verification appointments are often necessary with the patient present to verify the fit, the function and the esthetics. Digital two-dimensional photography has been helpful to minimize some of the difficulties, but has fallen short in alleviating many of the troublesome aspects of restoring these patients. Accurate analog impression materials have been developed that allow for precise capture and duplication of the dentition and the restorative components, but this technology still requires a series of laborious workflows to produce analog models and prostheses for the doctors and the laboratory technicians.

To replace a broken or damaged tooth, a dental implant is often placed in the location of the missing tooth or teeth. The implant will generally have a hexagonal shape to receive an impression coping and, subsequently, a dental prosthesis. After the implant has been inserted into the patient's mouth, the dentist will insert an impression coping into the implant for the purpose of registering the exact position of the implant in the patient's mouth.

Historically, the dentist will make a "pick-up" dental impression of the patient's mouth and impression coping(s). Once the impression material has hardened and the dental impression is complete, the dentist can remove the "pick-up" dental impression from the patient's mouth and effectively record the position of the implant(s). This can then be sent to a lab to create a dental mold, in stone form, of the patient's teeth.

A scan body, is an impression coping designed to be registered digitally as appointed to the aforementioned analog technique. The scan body is screwed into the dental implant in the patient's mouth and is scanned using a commercially available Intra-Oral Scanner (IOS). The scan body can be screwed into a Multi-Unit Abutment that is secured with a screw to the dental implant and utilized in the final prosthesis. The scan body can have an indexing means that can allow the CAD CAM program to determine the orientation and angle of the scan body relative to the hex shape on the dental implant, so that the CAD CAM program can design the implant prosthetic to be fitted precisely to the implant. Many of the currently utilized scan bodies have undercuts that are difficult to scan using an IOS and/or are large and bulky making it difficult to use in many situations in the mouth. Many scan bodies are difficult to fully scan with an IOS due to the size and shape of the scan body that prevents the IOS from recording fully the scan body. It is difficult to scan these scan bodies immediately after implants have been surgically placed due to the blood and saliva filled environment. The level of accuracy necessary to scan has been determined by many to be almost impossible at the time of surgery because the IOS cannot scan properly with open wounds. Further, all of the scan bodies currently utilized for digital impressions of dental implants require that the scan body be scanned in the mouth, which is sometimes difficult to acquire an accurate scan.

After the scan has been captured, the scan body must be removed from the mouth and a healing abutment or other prosthesis will be affixed to the implant or MUA. This requires the removal and replacement of small parts that can be inadvertently dropped into the patient's mouth.

In addition to the foregoing, issues arise when attempting to image a human face. The movement of numerous muscles of the face make the acquisition and the alignment of multiple images difficult, resulting in numerous inaccuracies and in some instances making alignment potentially impossible because of the multiple facial images with different expressions. Attempting to acquire and align multiple images consisting of different facial expressions further complicates this process.

A fiducial marker or fiducial is defined as an object placed in the field of view of an imaging system that appears in the produced image for use as a point of reference or a measure. It may be either something placed into or on the imaging subject, or a mark or set of marks in the reticle of an optical instrument. Current fiducial markers utilized for this purpose are attached to the face in areas that have some level of mobility, and therefore disrupt the alignment process.

Obtaining a reference for natural head posture is important two-dimensionally and three-dimensionally to enable appropriate design and alignment of two-dimensional photographs as well as three dimensional facial scans. The reference point becomes the "horizon" or the level to the horizon. Several devices have been developed and utilized to display the level of the face referenced to the level of the horizon in two-dimensional photographs to enable a design of the smile that is appropriate for the patient's natural head posture. With existing three-dimensional scans, the representation of the face and smile can be turned and tilted as it is 3D; however, without the use of a fiducial marker and some leveled reference point, the design maintains some degree of arbitrariness.

BRIEF SUMMARY

The present disclosure is directed to systems and methods to provide for dental reconstruction and restoration.

As technology advances, the opportunity arises to utilize digital scanning technology to minimize treatment time for the patients and the treating doctors. Digital scanning technology can produce similar results as analog technology and provide results that offer opportunity to use the captured data in ways that far exceed what can be produced with analog methods if and when the appropriate workflows are followed. Digital workflows allow for data to be digitally sent via the internet. This minimizes the cost and time necessary to provide dental restorations. Digital workflows now allow dental laboratories to provide restorations to dentist from anywhere in the world in a timely fashion.

The present disclosure provides a digital workflow process for providing a dental restoration that includes the following steps:

obtaining preoperative digital records and images;
  obtaining a full arch dental restoration design image;
  displaying the design image in 3D display format;
  preparing an Intra-Oral Scan (IOS) to create digital records, including:
    attaching at least one from among one or more implants;
    attaching of multi-unit abutments (MUAs) to the one or more implants;
    attaching healing abutments the MUAs;
    placing of scan bodies on the healing abutments, obtaining an intraoral scan (IOS) of the scan bodies, followed by removal of the scan bodies, obtaining putty impressions of healing abutments, and IOS scanning to create first clinical digital records;
  aligning the clinical digital records to the preoperative digital records and images and creating a CAD design of the prosthesis;
  manufacturing of the dental prosthesis using the CAD design;
  removing healing abutments from the MUAs and attaching the dental prosthesis with prosthetic screws to the MUAs and allowing tissue around the prosthesis to heal for 3 to 6 months;
  obtaining post-healing digital records by detaching the dental prosthesis from the MUAs, attach scan bodies onto the MUAs, placing scannable detection and registration (ScanDAR) material around each scan body, obtaining an IOS of the scan bodies, removing the ScanDAR material and the scan body, placing healing abutments on each MUA, taking a putty impression of the healing abutments and tissue, and obtaining an IOS to obtain the post-healing digital records;
  aligning the preoperative digital records, the clinical digital records, and the post-healing digital records and forming a dental restoration design; and
  manufacturing the dental restoration by using the dental restoration design.

The present disclosure also provides a digital workflow process for providing a dental restoration in a patient that includes the following steps:

a first appointment to obtain preoperative digital records and images;
  a first laboratory design to obtain a full arch dental restoration design with a customized smile and ideal bite relationship to enable patient visualization in 3D;
  a second clinical appointment to perform surgical procedures, including removal of one or more teeth, insertion of one or more implants, attachment of multi-unit abutments (MUAs) to the implants, and attachment of healing abutments the MUAs, the placing of scan bodies on the healing abutments, place scannable detection and registration (ScanDAR) material around each scan body and obtaining an intraoral scan (IOS) of the scan bodies, followed by removal of the scan bodies, and obtaining putty impressions of healing abutments that is then scanned with an IOS or 3D facial scanner to create digital records;
  alternatively, the surgical appointment could take place at the initial record gathering appointment;
  a second laboratory design to align the digital records from the first or second clinical appointment to the preoperative digital records and images obtained in the first clinical appointment and designing the prosthesis utilizing CAD software, then sending the CAD design to a CAM for manufacturing or 3D printed the dental prosthesis;
  a third clinical appointment to remove healing abutments from the MUAs and attaching the dental prosthesis with prosthetic screws to the MUAs and allowing tissue around the prosthesis to heal for 3 to 6 months;
  a fourth clinical appointment to obtain post-healing digital records, detach the dental prosthesis from the MUAs, attach scan bodies onto the MUAs, place scannable detection and registration (ScanDAR) material around each scan body, obtaining an IOS of the scan bodies, remove the ScanDAR material and the scan body, placing healing abutments on each MUA, taking a putty impression of the healing abutments and tissue, and obtaining an IOS or 3D facial scanner of the same;
  a third laboratory design to align the digital records from all the foregoing steps and form a dental restoration design therefrom, and then manufacturing the dental restoration from the dental restoration design; and
  a fifth clinical appointment to remove the healing abutments from the MUAs and attach the dental restoration with prosthetic screws to the MUAs.

In accordance with another aspect of the present disclosure, the foregoing digital workflow method also works without the healing abutments, utilizing instead the scan bodies that attach directly to the MUAs. The MUA scan bodies will be utilized for that workflow and the healing abutments would be placed after the impression process is completed.

As will be readily appreciated from the foregoing, the disclosed digital workflow process utilizes digital scanning technology to allow the treating doctors to diagnose and develop a treatment plan more efficiently, decrease the treatment times necessary to produce the desired treatment plan and minimize the number of appointments, without compromising the quality of the treatment or final outcomes. Beyond diagnosis and treatment planning, the disclosed digital workflows enable the treating doctors to be more efficient with their surgical techniques, allowing them to refine their current protocols, and improve the outcomes for all involved. Integrating the technology and the disclosed digital workflow with their surgical skill decreases surgical appointment times, benefiting both the patients and the doctors. Laboratory technicians also benefit from these disclosed workflows because they are able to utilize the full available technology and accurately and more efficiently design, verify digitally, reproduce digitally, and produce the final restorations.

The utilization of the disclosed workflows enables doctors and technicians to integrate the emerging digital technology into their practices, making the entire process from start to finish more efficient, less costly, and more acceptable to their patients.

In addition to the foregoing digital workflow, the present disclosure provides scan bodies, healing abutments, MUAs, screws, polishing protectors, and other tools and devices that are specifically designed to enhance the foregoing digital workflow process, including without limitation providing a scan body to be placed over the healing abutment, scanned for the digital impressions, and then removed without needing to remove the attached healing abutment, solving the aforementioned problems.

In accordance with another aspect of the present disclosure, a digital aligner device is provided. With the use of the Digital InstaRisa™ Aligner (DIA) device, a fiducial marker can be utilized two-dimensionally and three dimensionally to image the human face with multiple facial expressions without changing the position of the object relative to the fiducial marker. That is, the fiducial marker will remain constant and relative to the hard, unmovable aspects of the face, even when the facial muscles move from scan to scan as the facial expressions change. The DIA will also allow for a horizon level to orient the face and the smile in the patient's natural head posture. The human maxilla is affixed to the skull and the maxillary teeth are affixed to the maxilla. The DIA is secured to the maxillary teeth, or directly to the maxillary edentulous ridge in the event the patient has no remaining maxillary teeth, and remains affixed to the maxillary teeth or maxillary ridge regardless of the facial expression. While scanning the face, the DIA will also be scanned, which will allow all of the scans with multiple facial expressions to be aligned with the same exact reference position.

A leveling bubble is attached to the DIA and is utilized to demarcate the relative cant of the smile to the horizon. This leveling bubble will remain even with the horizon in each of the scans and allow each of the scans to be aligned accurately and with the same constant reference point. This will ensure the capture of the image is aligned accurately with each subsequent scan and within the same orientation, relative to the horizon.

BRIEF DESCRIPTION OF THE SEVERAL VIEWS OF THE DRAWINGS

The foregoing and other features and advantages of the present disclosure will be more readily appreciated as the same become better understood from the following detailed description when taken in conjunction with the accompanying drawings, wherein:

FIGS. 2A-2E illustrate a multi-unit abutment analog formed in accordance with the present disclosure;

FIGS. 3A-3G illustrate a multi-unit abutment coping scan body formed in accordance with the present disclosure along with an assembly of the coping scan body with the analog of FIGS. 2A-2E;

FIGS. 4A-4H illustrate a multi-unit abutment short scan body formed in accordance with the present disclosure along with an assembly of the short scan body with the analog of FIGS. 2A-2E;

FIGS. 5A-5E illustrate a fixed prosthetic healing abutment formed in accordance with the present disclosure;

FIGS. 6A-6E illustrate a healing abutment with concave conical end section formed in accordance with the present disclosure;

DETAILED DESCRIPTION

Figure 1:
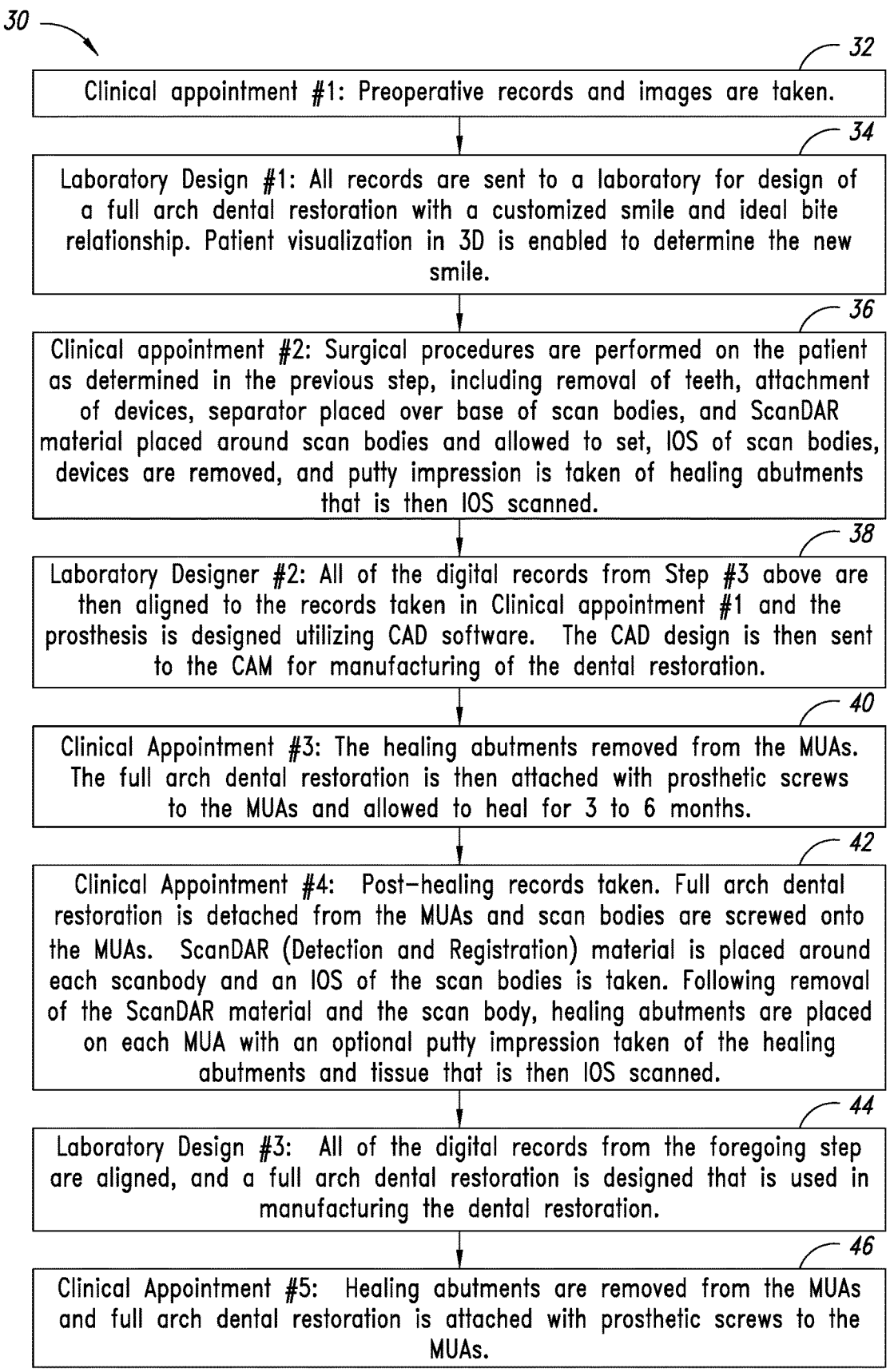
FIG. 1 is an illustration of work flow process formed in accordance with one implementation of the present disclosure.
Figure 2E:
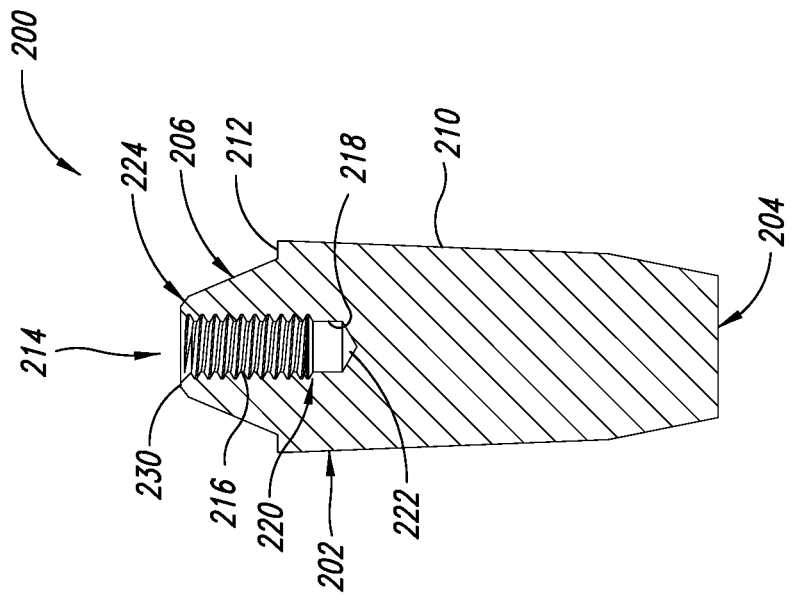
Figure 2D:
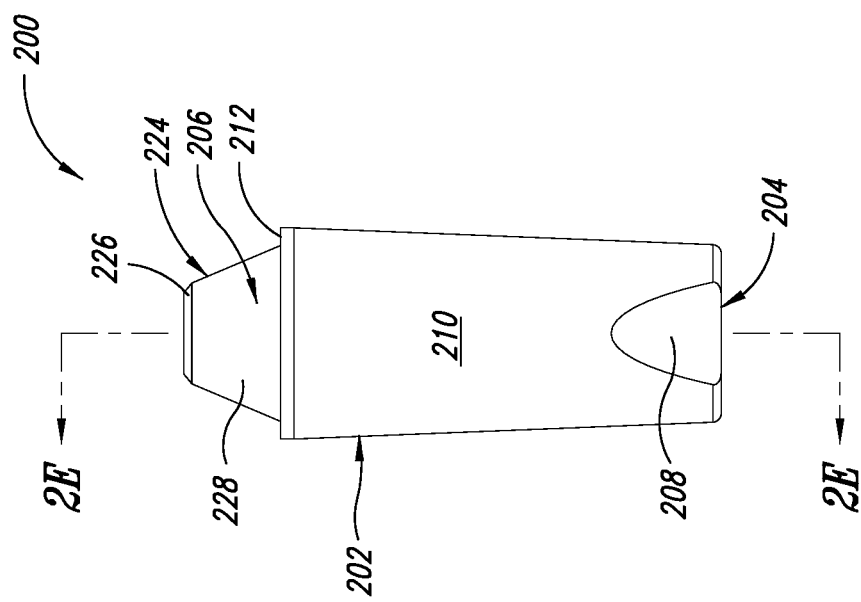
Figure 3G:
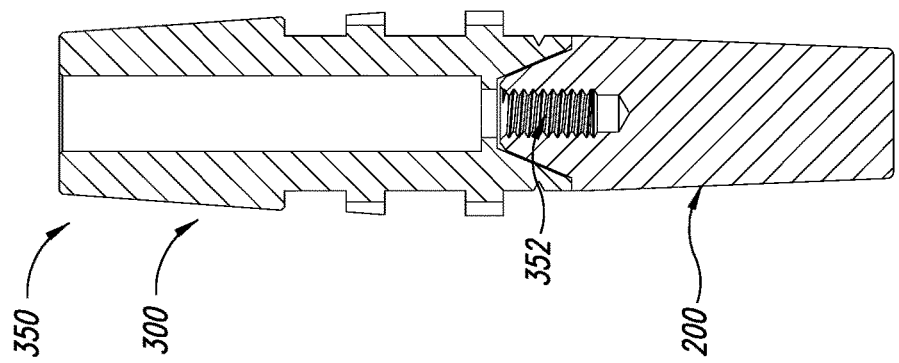
Figure 3F:
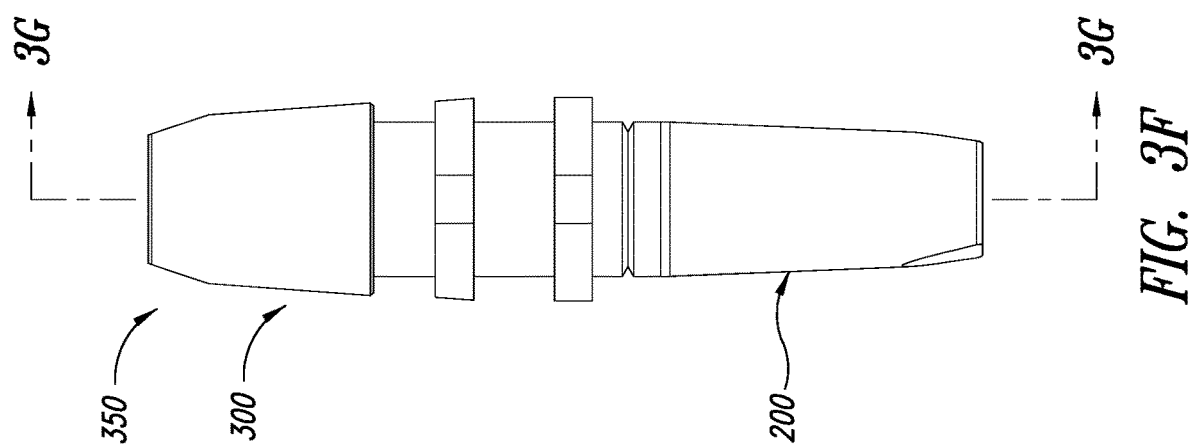
Figure 4E:
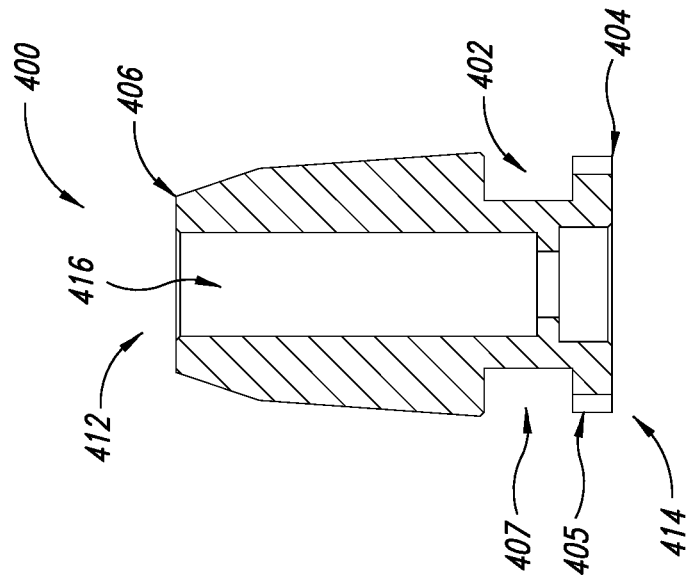
Figure 4D:
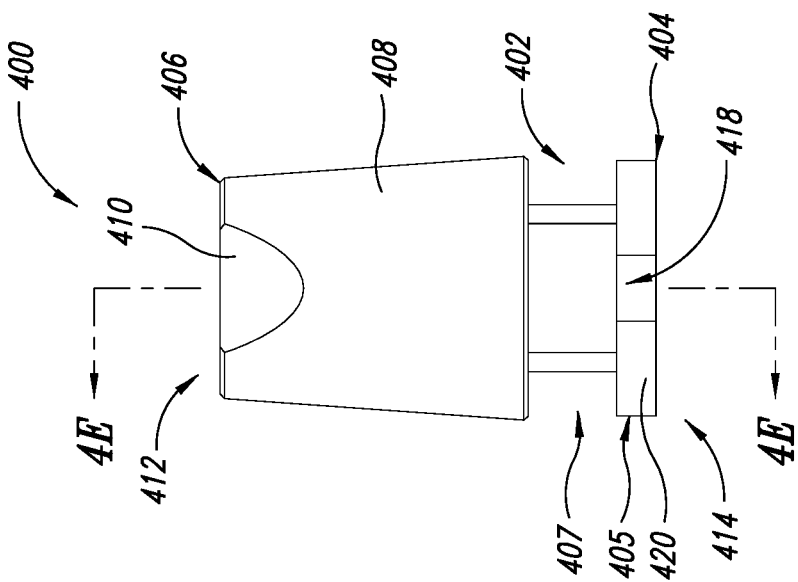
Figure 4H:
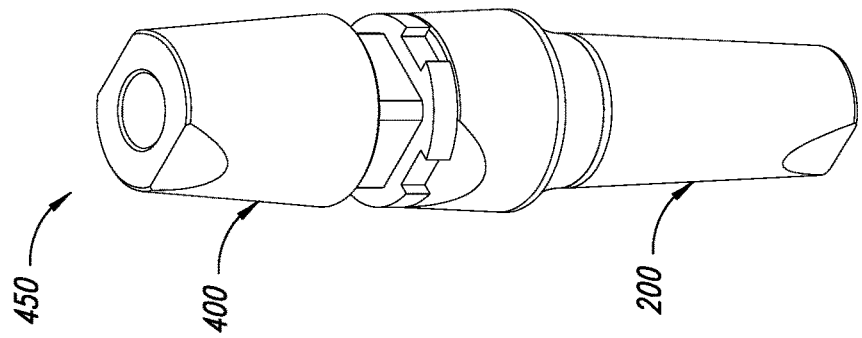
Figure 4G:
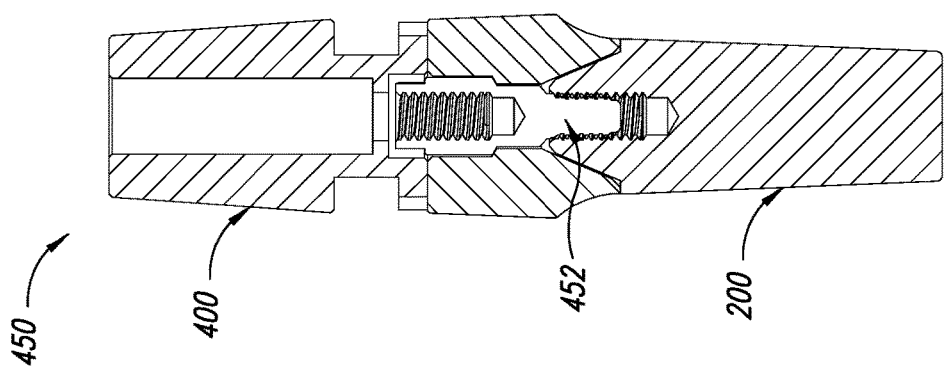
Figure 4F:
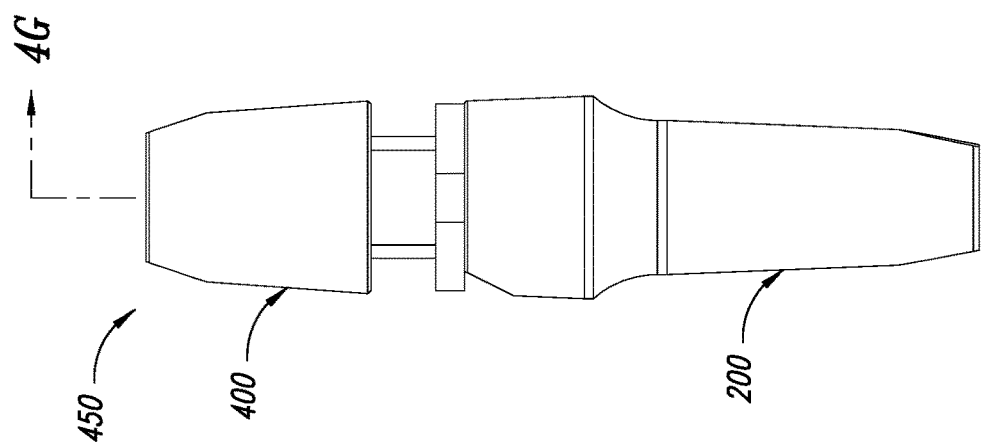
Figure 5E:
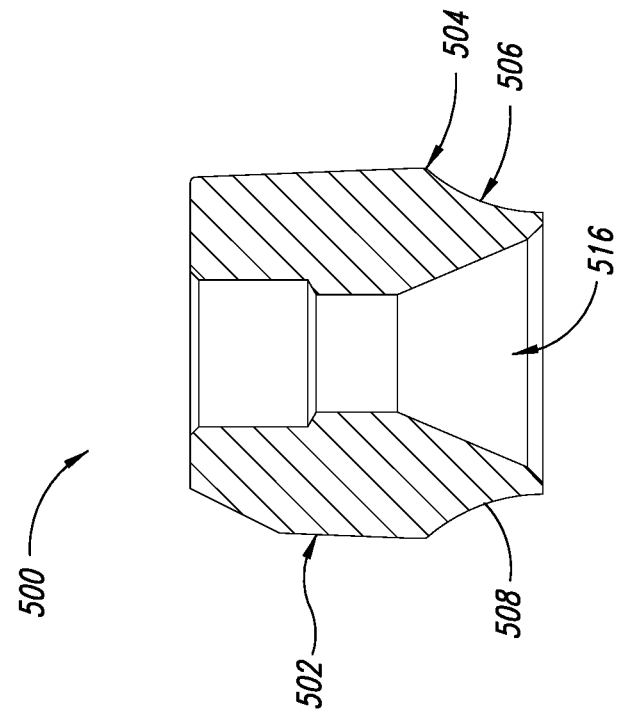
Figure 5D:
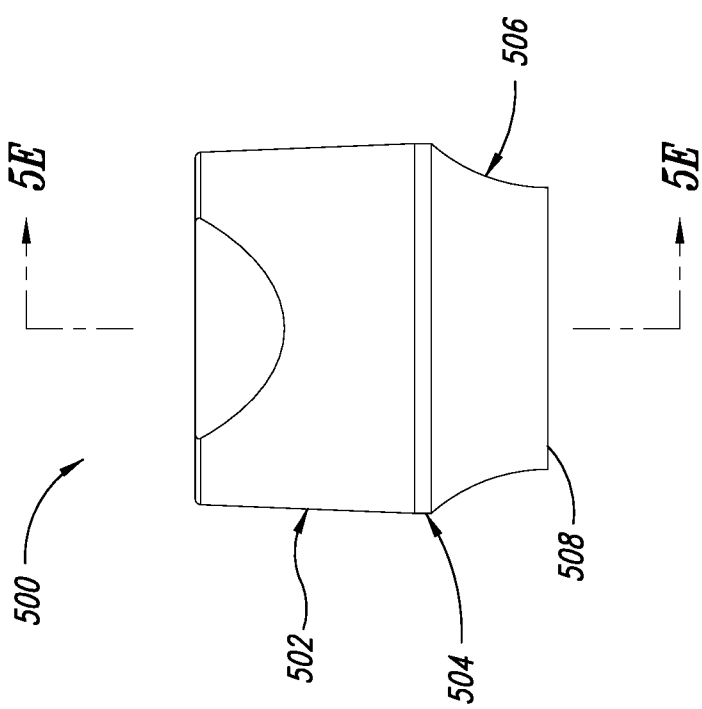
Figures 6D, 6E:
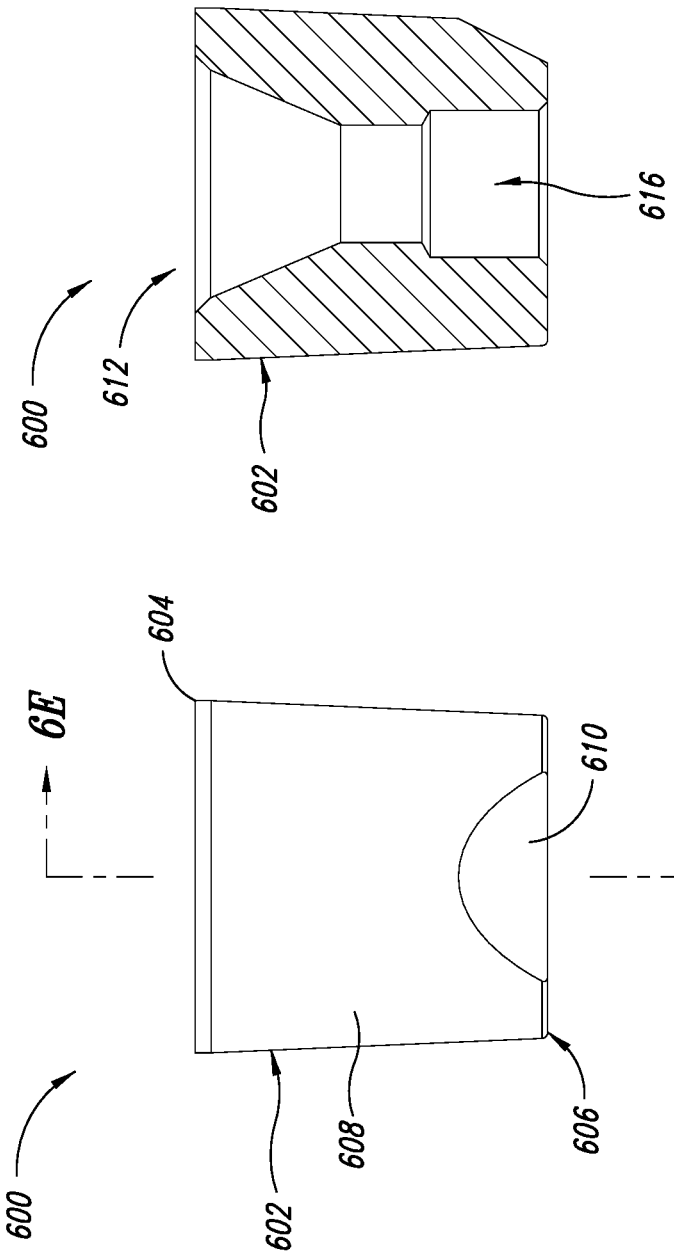
Figures 7A, 7B, 7C:
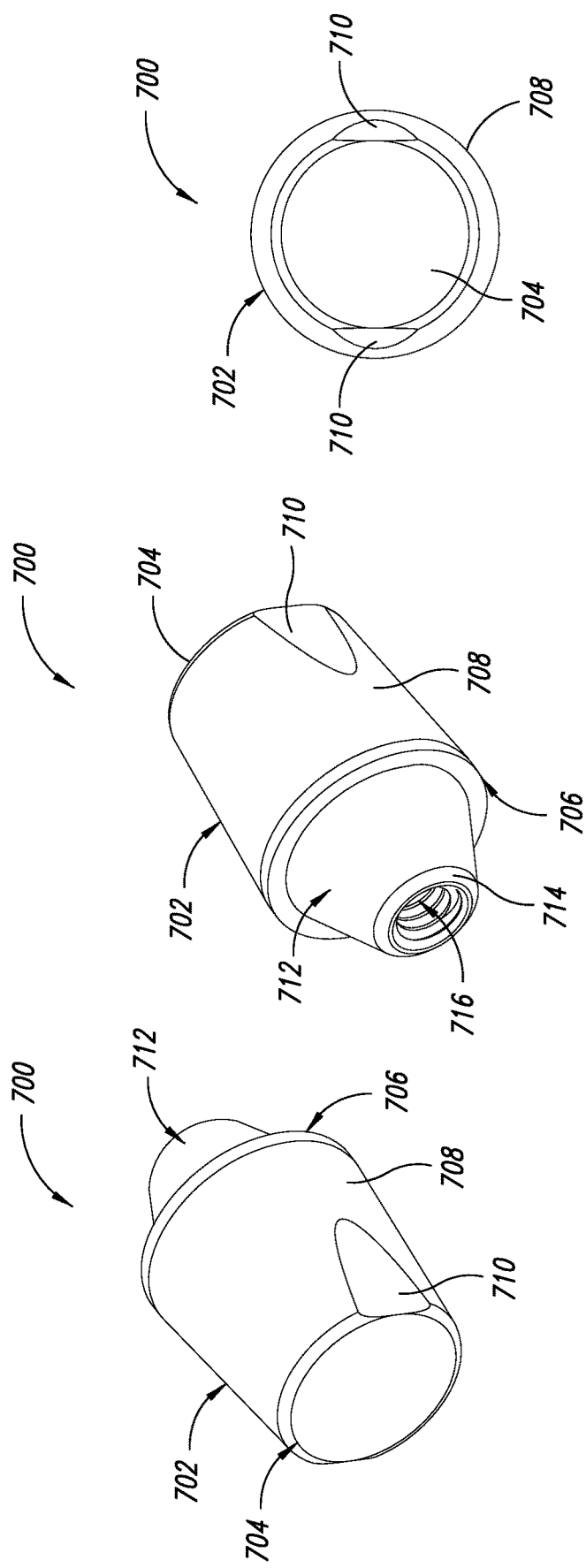
FIGS. 7A-7E illustrate a polishing protector formed in accordance with the present disclosure.
Figure 7E:
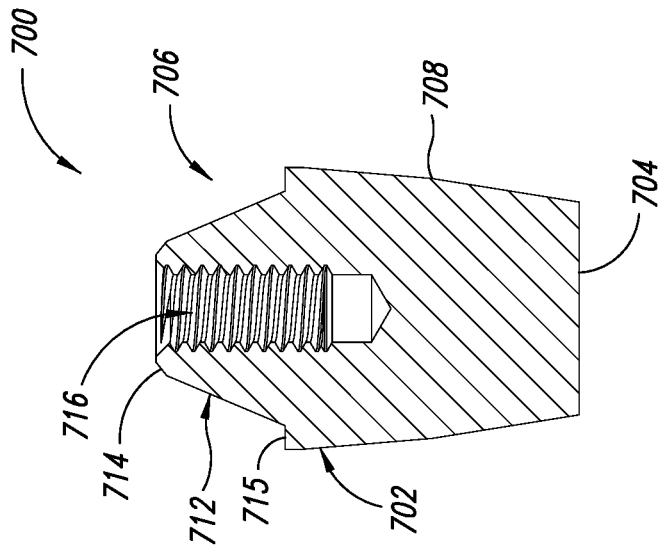
Figure 7D:
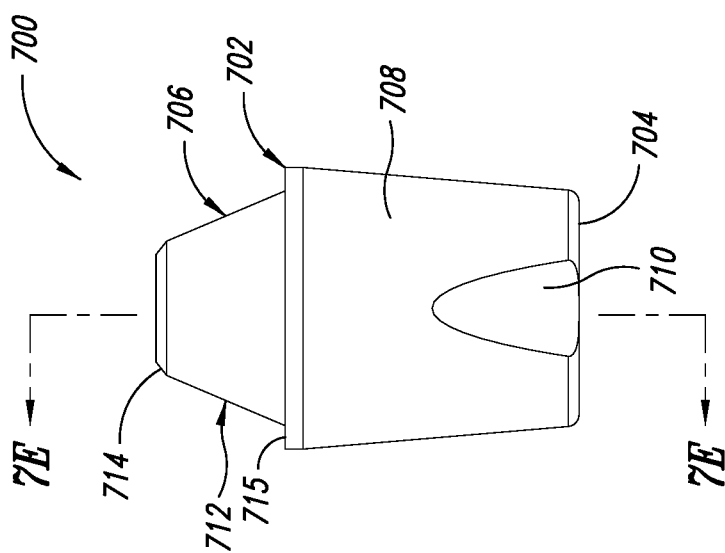
Figure 8A:
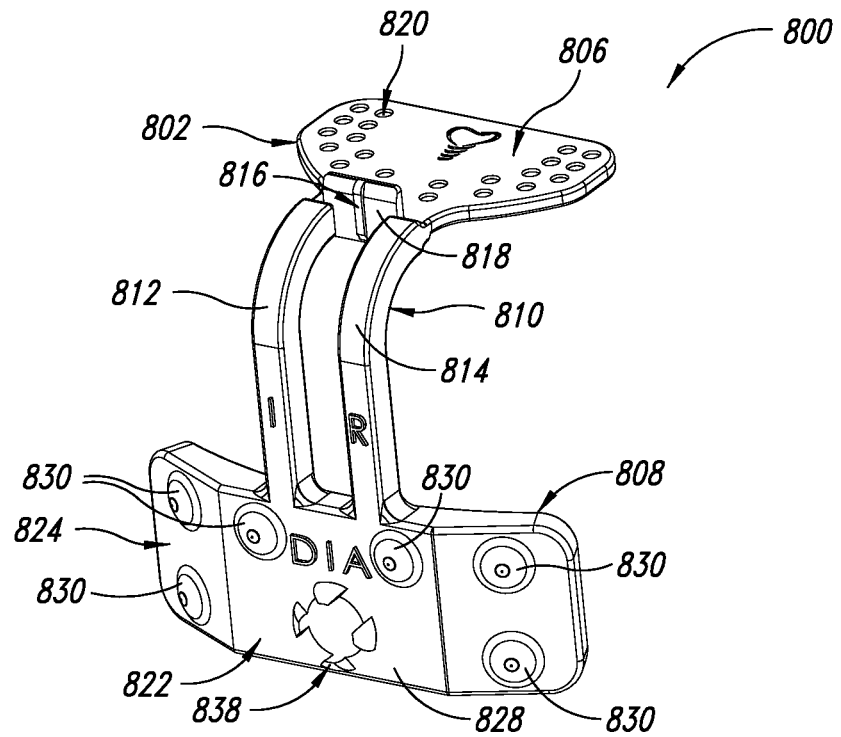
FIGS. 8A-8F illustrate an intraoral scan alignment assist device formed in accordance with the present disclosure.
Figure 8B:
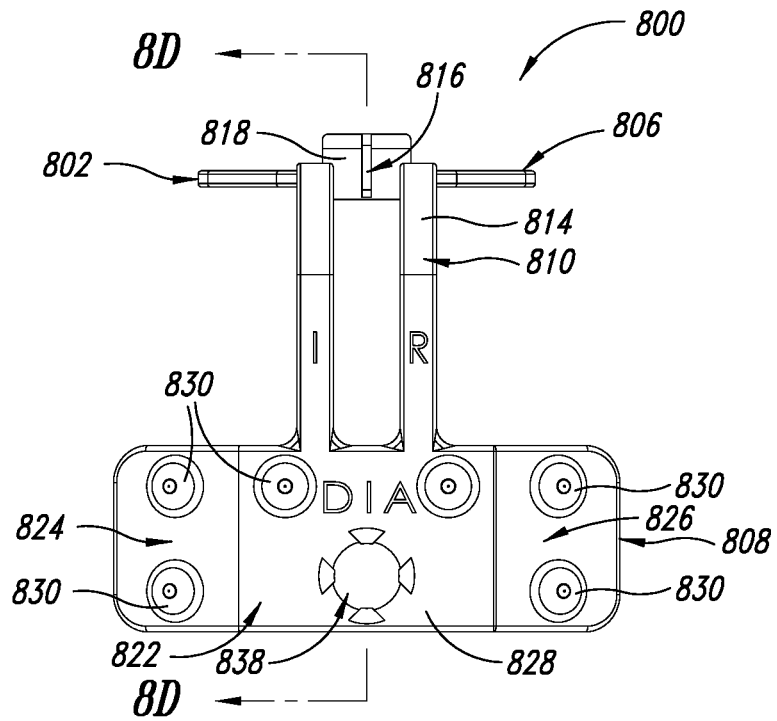
Figure 8C:
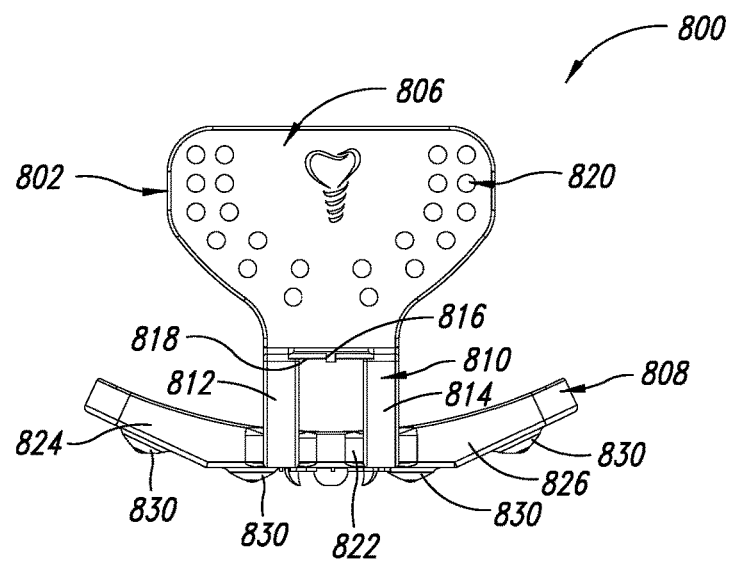
Figures 8D, 8E:
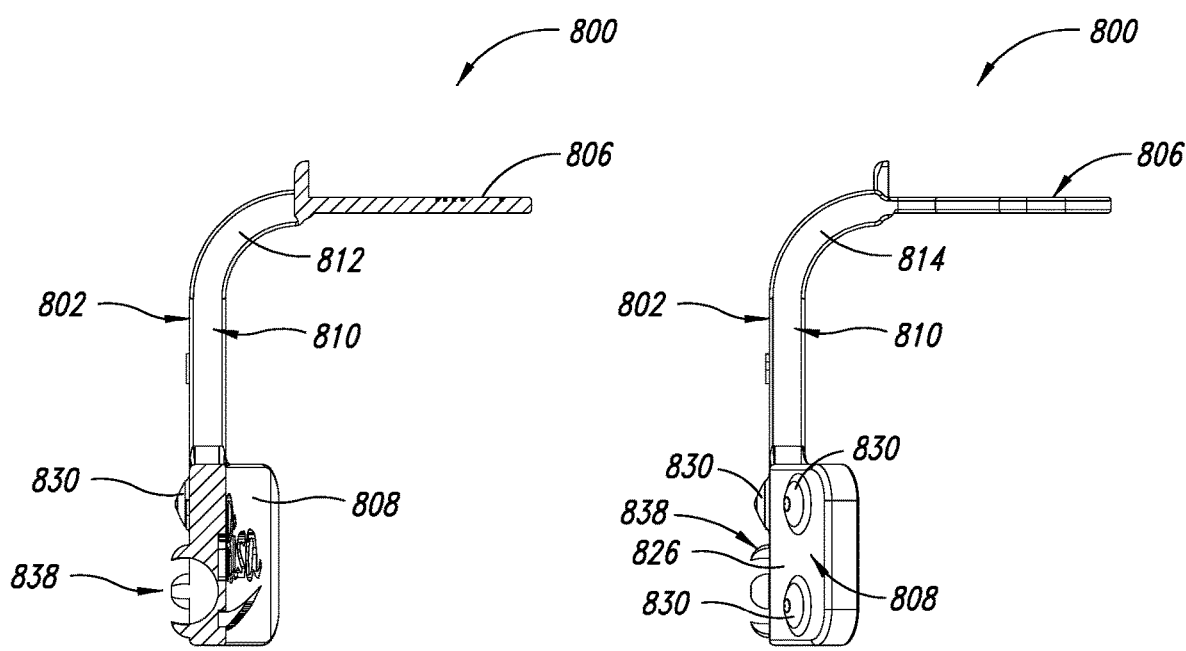
Figure 8F:
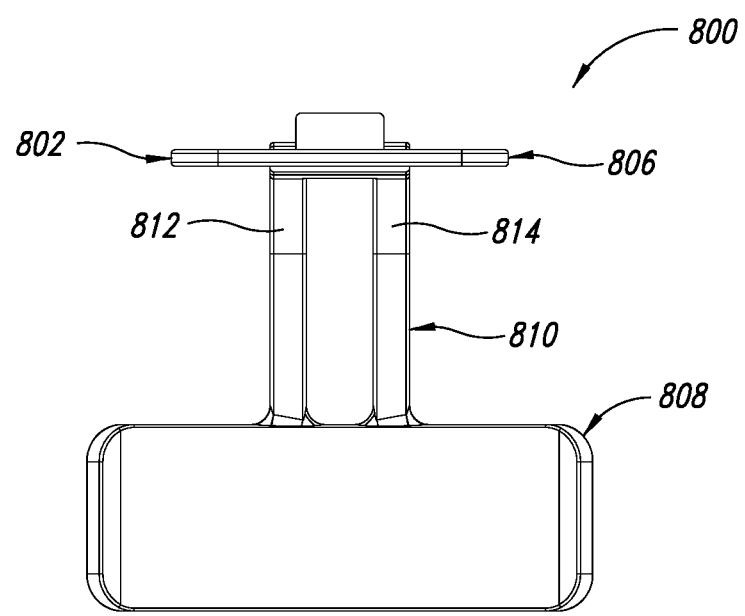
Figure 9A:
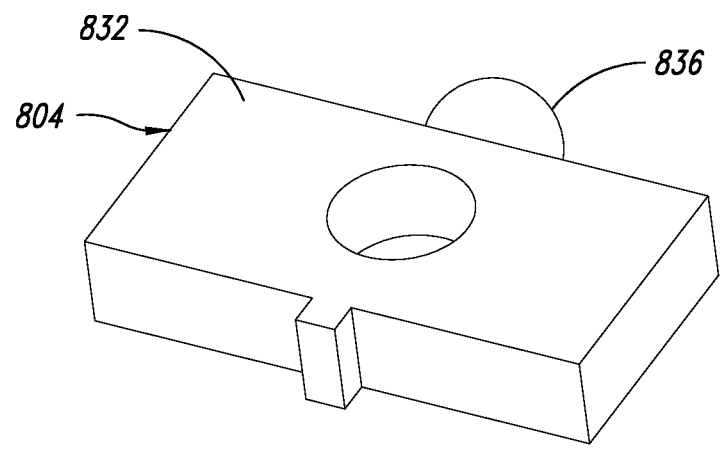
FIGS. 9A-9E illustrate a level device for use with the alignment assist device of FIGS. 8A-8G.
Figure 9B:
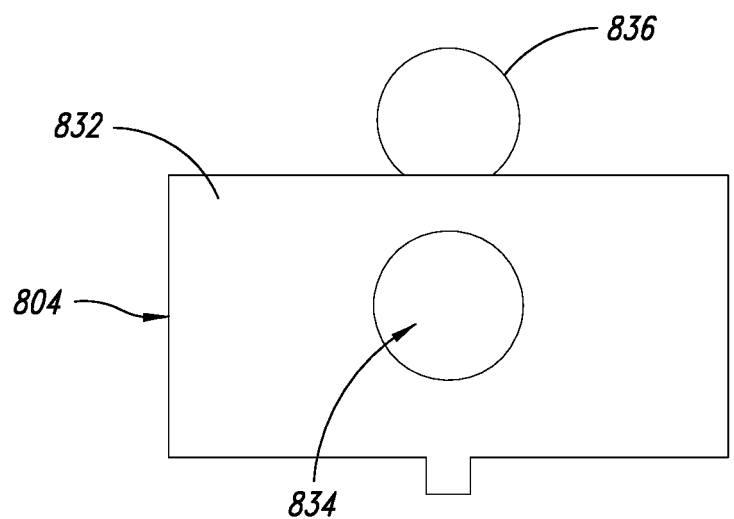
Figure 9C:
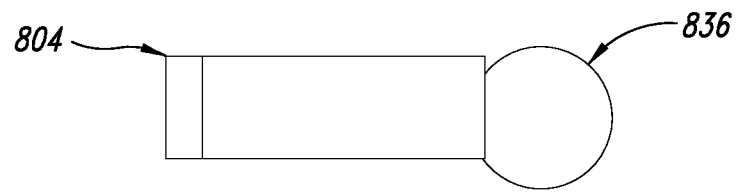
Figure 9D:
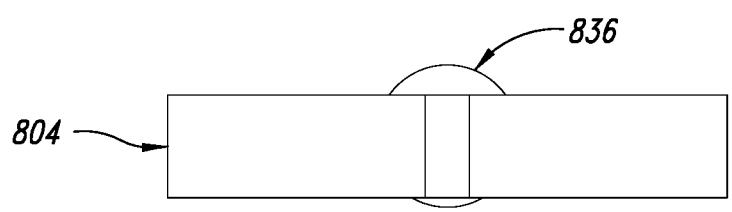
Figure 9E:
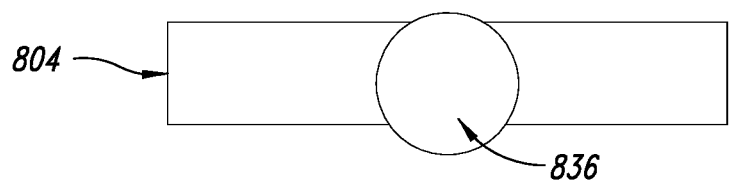

In the following description, certain specific details are set forth in order to provide a thorough understanding of various disclosed implementations. However, one skilled in the relevant art will recognize that implementations may be practiced without one or more of these specific details, or with other methods, components, materials, etc. In other instances, well-known structures associated with scanners, scan bodies, dental tools and devices have not been shown or described in detail to avoid unnecessarily obscuring descriptions of the implementations.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one implementation" or "an implementation" means that a particular feature, structure or characteristic described in connection with the implementation is included in at least one implementation. Thus, the appearance of the phrases "in one implementation" or "in an implementation" in various places throughout this specification are not necessarily all referring to the same implementation. Furthermore, the particular features, structures, or characteristics may be combined in any suitable manner in one or more implementations. It will be appreciated that for simplicity and clarity of illustration, where considered appropriate, reference numerals may be repeated among the figures to indicate corresponding or analogous elements or steps.

As used in this specification and the appended claims, the singular forms "a," "an," and "the" include plural referents unless the content clearly dictates otherwise. It should also be noted that the term "or" is generally employed in its broadest sense, that is as meaning "and/or" unless the content clearly dictates otherwise.

The headings and Abstract of the Disclosure provided herein are for convenience only and do not interpret the scope or meaning of the implementations.

General Overview

Restorative dentistry involves replacing or restoring missing teeth or parts of the tooth structure, including the use of fillings, crowns, bridges, implants, and dentures. Providing dental implants is a complex procedure involving a number of steps. These steps include placing an implant in the tooth root location for the replacement tooth, referred to herein as a prosthesis, then attaching a healing abutment to the implant, and allowing the gum tissue to heal around the site. The healing abutment is then replaced with a definitive abutment that becomes the connecting piece between the implant and the prosthesis. Healing abutments can be placed at the same time as the implant or during a second procedure following placement of the implant.

Accuracy when restoring implants has long been known to be a key factor in implant survival and esthetics. Poorly fitting restorations and abutments can lead to implant and restoration failure. There are many steps involved in the traditional implant impression, and each step incrementally adds to increased distortion of the final restoration.

To ensure accurate placement of the implant in the jaw bone, a scan body (also known as an intraoral scan body (ISB)) is temporarily attached to the implant prior to imaging of the devices, such as with an intraoral scan (IOS). ISBs are essential implant-positioning devices that have become essential tools in the advancement of digital workflow and fabrication of accurately placed and fitted prostheses.

Once the dental implant is placed into the jaw bone in the position of the missing tooth, the MUA is secured on and into the dental implant. The scan body is designed to inversely replicate the MUA and is secured with a fixation screw onto the MUA. The scan body is then captured digitally with an IOS that captures the exact position of the scan body, which in-turn registers the exact position of the MUA and consequently registers the exact position of the dental implant. The configuration and geometry of the scan body allows for an accurate scan of the scan body and allows for a more efficient scan due to the design. In the event that a complete and accurate IOS proves difficult or impossible, the scan body is configured with retentive features to allow for the fixation of one scan body to another with a rigid material that will enable removal of the scan bodies from the mouth and scanned extra-orally while maintaining the exact position relative to one another. This process enables the merging of the IOS and extra-oral scans and fabrication of the desired dental prosthesis with an accurate fit to the MUA and dental implant in the mouth.

As scanner technology evolves, the design and use of implants, abutments, scan bodies, and related devices must likewise evolve. Described below is a novel adaption and improvement of both a digital workflow process and the tools and devices used in the disclosed workflow process.

Digital Workflow Description

The process for providing a dental implant or dental prosthesis and then a dental restoration generally includes the following steps:
 obtaining preoperative digital records and images;
 obtaining a full arch dental restoration design image;
 displaying the design image in 3D display format;
 preparing an Intra-Oral Scan (IOS) to create digital records, including:
  attaching at least one from among one or more implants;
  attaching of a multi-unit abutment (MUA) to each of the one or more implants;
  attaching a healing abutment to each MUA;
  placing of a scan body on each healing abutment, obtaining an intraoral scan (IOS) of the scan body, followed by removal of the scan body, obtaining putty impressions of the healing abutment, and IOS scanning to create a clinical digital records;
  aligning the clinical digital records to the preoperative digital records and images and creating a CAD design of the prosthesis;
 manufacturing of the dental prosthesis using the CAD design.

The process continues with the dental prosthesis being installed by removing healing abutments from the MUAs and attaching the dental prosthesis with prosthetic screws to the MUAs and allowing tissue around the prosthesis to heal for 3 to 6 months.

After the healing process of 3 to 6 months, the process for manufacturing the dental restoration would include obtaining post-healing digital records by detaching the dental prosthesis from the MUAs, attach scan bodies onto the MUAs, placing scannable detection and registration (Scan-DAR) material around each scan body, obtaining an IOS of the scan bodies, removing the ScanDAR material and the scan body, placing healing abutments on each MUA, taking a putty impression of the healing abutments and tissue, and obtaining an IOS to obtain the post-healing digital records.

The next step in manufacturing the dental restoration includes aligning the preoperative digital records, the clinical digital records, and the post-healing digital records and forming a dental restoration design. After this the manufacturing of the dental restoration is done by using the dental restoration design.

What follows next is a digital work flow process formed in accordance with a representative embodiment of the present disclosure.

Referring to FIG. 1, shown therein is a digital work flow process 30 formed in accordance with one implementation of the present disclosure. Digitizing the patient with Facial Scanner (FS) data combined with IOS data allows the dentist and CAD CAM laboratory technicians to provide dental restorations that fit dental implants precisely with optimal form and function. The digital workflow 30 combines technology and equipment as follows:

In an initial step 32, a first clinical appointment takes place. Preoperative records of the patient are taken, including without limitation a Cone-beam Computed Tomography (CBCT) scan of the maxilla and mandible, IOS of the maxilla and mandible, FS of the bite with lip retractors, FS with lips in repose, FS with natural smile, and FS with Duchenne (exaggerated) smile.

In the next step 34, the records obtained in the initial step 32 are sent to a Laboratory Designer. All records are aligned in CAD software and the CAD designer takes all extra-oral and intra-oral landmarks anatomical into consideration in order to then create a pre-surgical dental restoration design. Within this workflow, with the FS and IOS records taken into consideration, a full arch dental restoration with a customized smile with an ideal bite relationship is now designed. The amount of bone present and if necessary the amount of bone reduction is determined, which allows for dental implant planning capabilities. A visualization of the patient's face and smile is created for patient review. Patients visualize their new smile in 3D, virtually. This enables patients to modify or accept their new smile prior to surgery.

In the event that the patient or the doctor desire to modify the virtual design, these changes can be made digitally at that instant, or communicated to the laboratory or designer who can make the modifications to the design. Once the design is approved, the next steps can be implemented.

Once the new smile is determined, the next step 36 involves a second clinical appointment at which time the surgical procedures are performed. This can involve removal of one or more teeth, gingival tissue, and bone, the quantity of which was determined in step 34 above. Implants are placed, Multi-Unit Abutments (MUA) are attached to the implants, and scan bodies are screwed into the MUAs. A separator is placed over the base of the scan bodies to prevent saliva and blood from getting onto scan body or in field of scan capture, and ScanDAR (Detection And Registration) material is placed around each scan body and allowed to set. An IOS of the scan bodies is then taken. The ScanDAR and scan bodies are then unscrewed and removed from the MUAs. Healing abutments are then placed on each MUA and soft tissue is sutured. A putty impression is taken of the healing abutments and tissue and allowed to set. Once the putty material is set, it is removed from the patient's mouth and scanned with an IOS to capture the intaglio surface that is not predictably scanned intra-orally Because the soft tissue is traumatized at this point from surgically removing teeth and placing implants, it is not static. An IOS only tracks and stitches static images together, so the ScanDAR allows for the IOS to track and stich images very predictably.

In step 38 all of the digital records from step 34 above are then aligned to the records taken in the first clinical appointment of step 32. Following alignment, the prosthesis is designed from the first laboratory designer of step 34 utilizing CAD software. The CAD design is then sent to the CAM for manufacturing of the dental restoration. The full arch dental restoration is then polished, stained, and glazed to create a natural set of bridged teeth.

In the next clinical appointment in step 40, the healing abutments are then removed from the MUAs. The full arch dental restoration is attached with prosthetic screws to the MUAs. The dental implants are then allowed to heal, which involves osseointegration for a period of 3-6 months.

The patient returns for the follow-up clinical appointment in step 42 where post-healing records taken. These can include one or more of the following: an IOS of the upper and lower arch, FS of the bite with lip retractors, FS with lips in repose, FS with natural smile, and FS with Duchenne (exaggerated) smile. The full arch dental restoration is then unattached from the MUAs, and scan bodies are screwed onto the MUAs. ScanDAR (Detection And Registration) material is placed around each scan body and allowed to set, then an IOS of the scan bodies is taken. The ScanDAR and scan bodies are then removed from the MUAs. Healing abutments are placed on each MUA followed by either an IOS or a putty impression of the healing abutments and tissue. If the putty impression was acquired, then it is scanned with an IOS.

All of the digital records from step 42 above are then aligned at the laboratory in step 44, and a new full arch dental restoration is then designed with CAD software. The CAD design is then sent to the CAM for manufacturing of the dental restoration. The full arch dental restoration is then polished, stained and glazed to create a natural set of teeth.

In the final clinical appointment of step 46, the healing abutments are removed from the MUAs, and the full arch dental restoration is attached and retained with prosthetic screws to the MUAs.

The digital workflow 30 is now complete.

Digital Workflow Devices and Tools

In accordance with another aspect of the present disclosure, various devices and tools have been designed to enhance the digital work flow 30 described above.

FIGS. 2A-2E illustrate a multi-unit abutment analog 200 formed in accordance with the present disclosure is provided. The abutment 200 includes an elongated, generally cylindrical body 202 having a substantially planar first end 204 and a conical opposing second end 206. Ideally the body 206 has a truncated conical configuration with the diameter at the first end 204 smaller than a diameter at a beginning of the conical second end 206.

The first end 204 has two mutually opposing oblique faces 208 formed in a sidewall 210 of the body 202 that extend from the first end 204 onto the body sidewall 210 towards the second end 206 about 20% to 30% of the distance between the first and second ends 204, 206 of the body 202. The conical second end 206 has a diameter smaller than a diameter of the body 202 to form a substantially orthogonal annular shoulder 212 around the entire diameter of the body 202 where the conical second end 206 joins the body 202.

A stepped internal axial bore 214 is formed in the body 202 that opens to the conical second end 206 and terminates about one-third of the way into the body 202. The bore 214 has a first section 216 having a first diameter and a second section 218 of a smaller diameter that forms a shoulder 220. The bore 214 terminates in a conical shaped terminus 222. The bore 214 may be formed with internal threads to facilitate attachment to other devices.

The conical second end 206 may have its end 224 chamfered to form a surface 226 that has a steeper angle of diminishing radius than the main section 228 from which it extends. Ideally the conical second end 206 has a flat orthogonal annular surface 230 at its terminal end.

FIGS. 3A-3G illustrate a multi-unit abutment coping scan body 300 formed in accordance with the present disclosure along with an assembly of the coping scan body with the analog of FIGS. 2A-2E, and FIGS. 4A-4H illustrate a multi-unit abutment short scan body 400 formed in accordance with the present disclosure along with an assembly of the short scan body with the analog of FIGS. 2A-2E. The scan body 300, 400 is designed for a dental impression and contains a base 302, 402 with a coupling geometry 304, 404 configured to fit a geometry of a dental implant coupling as described more fully below, and a body 306, 406 with lateral surfaces 308, 408 configured with one or more geometrical elements 310, 410, in this case one or more oblique faces, that allow identification of position, direction and rotation.

Ideally, the scan body 300, 400 has a widening shape from a top 312, 412 to a bottom 314, 414 to enable capturing the entirety of the scan body 300, 400 with the IOS. The scan body 300, 400 further includes a longitudinal axial bore 316, 416 that extends completely through the body 306, 406, and opens at the top 312, 412 and bottom 314, 414, preferably with internal threads (not shown) to receive a fixing screw (not shown) that is threadably inserted therein.

The scan body 300, 400 is designed with the coupling geometry 304, 404 to enable accurate scan alignment with multiple scans, intra-oral and extra-oral, allowing for accuracy of fit of any and all prostheses fabricated from these scans to fit the specific implant position within the patient's mouth. More particularly, the geometry 304, 404 includes one or more encircling or annular geometrical shapes 305, 405 with one or more channels 307, 407 that are designed to capture and secure a settable fluid material (not shown) that is flowed around the base and secured around the base 302, 402, creating a mechanical means of retention of the material once it sets and becomes rigid.

In addition, longitudinal grooves 318, 418 are formed within the exterior surface 320, 420 of the annular geometric shapes 305, 405 that are configured for anti-rotation of the aforementioned material and subsequently the scan body 300, 400 itself within the material. Further, the channels 307, 407 are sized and shaped to allow for and enable dental floss or some other similar material to be wrapped around each scan body 300, 400 and enable it to remain secured while simultaneously wrapping around and adjoining any other adjacent implant scan bodies within the arch. The previously mentioned material will be flowed around the scan bodies 300, 400 in the same manner as previously described and around the floss to create more stability and rigidity between and around the scan bodies.

Preferably, and as shown most clearly in FIG. 3D, in the longer scan body 300 there is a groove 322 created around the circumference of the bottom 314 that creates lip 324 for retention of a flat latex or similar material piece, often in a circular shape, to serve as a barrier between the tissue and blood and sulcular fluids, i.e., the surgical field, to prevent these fluids from interfering with the set and retention of the material that is flowed around the scan bodies, as well as to prevent blood and saliva from entering onto the primary scanning portion of the scan body. If and when those fluids come into contact with the scan body, the scanning becomes more difficult as the IOS has difficulty "reading" the scan body through the fluid.

The scan bodies 300, 400 are designed to connect directly to a Multi-Unit Abutment (MUA), such as the MUA analog 200 describe above with respect to FIGS. 2A-2E or the abutments described further herein below, which is affixed to the dental implant and remains as a component of the definitive restoration. These assemblies 350, 450 are shown in FIGS. 3F-3G and FIGS. 4F-4H respectively. In the cross section views of FIGS. 3G and 4G, a fastener 352, 452 holds the two components 300, 200 and 400, 200, respectively, together. Ideally the fastener 352, 452 has threads to engage with corresponding threads in each of the components 200, 300, 400 to enable threadable engagement and disengagement of the respective components 200, 300, 400. In one aspect of the present disclosure, the fastener 352, 452 may be formed as part of the scan body 200, 300 or the analog 200, although in the representative embodiment it is shown as a discrete component 352, 452.

As will be readily appreciated from the foregoing, the scan body 300, 400 contains retentive features 305, 307 and 405, 407 at the base of the scan body 300, 400 designed to be captured by an impression material to enable scanning extra-orally in the event the IOS is difficult or impossible with current technology. The scan body 300, 400 also contains areas that allow several methods of fixation to be applied to each scan body, fixing the position of each individual scan body relative to an adjacent scan body.

The features mentioned above allow for an easier and more efficient digital capture of the scan body and subsequently the MUA and dental implant to which it is affixed. The incorporation of additional geometry that employs specifically designed undercuts 320, 420, as well as the oblique faces 310, 410, at the base of the scan body 300, 400 allow for several methods of accurate scan capture of these scan bodies in the event the IOS proves difficult or impossible, a method previously not available.

Referring next to FIGS. 5A-5E, illustrated therein is a healing abutment 500 with main body 502 and tapered end section 504 having concave side walls 506 formed in accordance with the present disclosure. The main body 502 has a truncated conical shape that tapers in diameter from its greatest diameter adjacent the end section 504 to a smallest diameter at a truncated end 508. A single oblique face 510 is formed in a circumscribing sidewall 512 of the body 502 adjacent the truncated end 508. An annular recess 512 is formed inside the body 502 that opens to the tapered end section 504. A central axial opening 516 opens into the body 502 from the truncated end 508 that may have internal threads (not shown). Two shallow openings 517 are formed in the truncated second end 508.

FIGS. 6A-6E illustrate a fixed prosthetic healing abutment 600 formed in accordance with the present disclosure having a main body 602 with a first end 604 and opposing second end 606. The main body 602 has a circumscribing sidewall 708 with a truncated conical shape that tapers in diameter from its greatest diameter at the first end 604 to a smallest diameter at the second end 606. A single oblique face 610 is formed in the sidewall 608 of the body 602 adjacent the second end 606. An annular recess 612 is formed inside the body 602 that opens to the first end section 604. A central axial opening 616 opens into the body 602 from the second end 606 that may have internal threads (not shown). Two shallow openings 617 are formed in the second end 606.

FIGS. 7A-7E illustrate a polishing protector 700 formed in accordance with the present disclosure having a main body 702 with a first end 704 and opposing second end 706. The main body 702 has a circumscribing sidewall 708 with a truncated conical shape that tapers in diameter from its greatest diameter at the second end 706 to a smallest diameter at the first end 706. A pair of opposing oblique faces 610 are formed in the sidewall 708 of the body 702 adjacent the first end 704. A conical extension 712 extends from the second end 704 with a reducing diameter from the intersection with the second end 704 to a chamfered tip 714. The diameter of the conical extension 712 where it meets the second end 704 of the body 702 has a smaller diameter than the second end 074 of the body 702, thus forming a shoulder 715 orthogonal to the conical extension 712. A central axial opening 716 opens into the body 702 at the second end 706 that may have internal threads (not shown).

FIGS. 8A-8F illustrate an intraoral digital scan alignment assist system 800 formed in accordance with the present disclosure. The alignment system 800 is constructed in two parts, which can be made of 3D printed resin. The first part is a bite platform aligner 802, referred to at times herein as an aligner or DIA device 802, and the second part is a natural head position aligner or leveling device 804.

As shown in FIGS. 8A-8F, the aligner DIA device 802 has three main structural components including a platform 806, an alignment plate 808, and a bent frame 810 that connects the platform 806 to the alignment plate 808. The bent frame 810 consists of two legs 812, 814 that are bent to a 90 degree or right angle near a top adjacent a connection to the platform 806. This bend is outward when the DIA device 802 is in the patient's mouth to avoid interference with the lips and enable capturing of the natural lip position. A midline ridge 816 is formed on a proximal side wall 818 of the platform 806 to aid in lining up the DIA device 802 with the patient's midline. In use, ScanDAR material (not shown) is placed on a top surface of the platform 806, and the patient bites into the material. As the material hardens, it stabilizes the DIA device 802 in the patient's mouth. One or more openings 820 are provided in the platform 806 to aid in retaining the ScanDAR material on the platform 806. The alignment plate 808 has a center section 822 with wings 824, 826 extending from each side. On an exterior side 828 of the plate 808 are a plurality of alignment domes 830 are formed to allow the DIA device 802 to be accurately aligned with other DIA facial scans in the CAM software.

With the use of the DIA device 802, a fiducial marker can be utilized two-dimensionally and three dimensionally to image the human face with multiple facial expressions without changing the position of the object relative to the fiducial marker. The fiducial marker, in this case the DIA device 802, will remain constant and relative to the hard, unmovable aspects of the face, even when the facial muscles move from scan to scan as the facial expressions change. The DIA device 802 provides for a horizon level to orient the face and the smile in the patient's natural head posture.

The human maxilla is affixed to the skull and the maxillary teeth are affixed to the maxilla. The DIA device 802 is secured to the maxillary teeth, or directly to the maxillary edentulous ridge in the event the patient has no remaining maxillary teeth and remains affixed to the maxillary teeth or maxillary ridge regardless of the facial expression. While scanning the face, the DIA device 802 will also be scanned, which will allow all of the scans with multiple facial expressions to be aligned with the same exact reference position.

A leveling bubble device 804 shown in FIGS. 9A-9E is attached to the outer surface 828 of the plate 808 of the DIA device 802. It is utilized to demarcate the relative cant of the smile to the horizon. The bubble device 804 has a rectilinear shape with a top surface 832 in which is formed an indentation or opening 834 to which a bubble level (not shown) is attached. A spherical attachment ball 836 depends from a side wall and is sized and shaped to attach to and rotate on a receiver 838 on the plate 808. This leveling bubble device 804 will remain even with the horizon in each of the scans and enable each of the scans to be aligned accurately and with the same constant reference point. This will ensure the capture of the image is aligned accurately with each subsequent scan and within the same orientation, relative to the horizon.

In use, ScanDAR (Detection and Registration) material is placed on the bite platform 808 of the DIA device 802 and inserted into the mouth. The patient is asked to bite down onto the bite platform 806 of the DIA device 802, and the ScanDAR material is allowed to completely set to a rigid form. In order to determine natural head posture, a full sized mirror is placed in front of the patient, and the patient is instructed to look into it. This will naturally place the patients head in a natural head position. The leveling bubble device 804 is then oriented to the center, so it is level to the horizon. The patient is asked to create the following facial expressions, and each one is individually scanned with a facial scanner: Natural smile, Duchenne (exaggerated) smile and Repose (a relaxed lip position). All 3D facial scans are exported to CAD software where they are all aligned to one another with the DIA device 802 as the fiducial marker. This process allows for a very accurate, fast, and simple method for 3D facially generated smiles with different facial expressions.

These and other changes can be made to the implementations in light of the above-detailed description. In general, in the following claims, the terms used should not be construed to limit the claims to the specific implementations disclosed in the specification and the claims, but should be construed to include all possible implementations along with the full scope of equivalents to which such claims are entitled. Accordingly, the claims are not limited by the disclosure.

The invention claimed is:

1. A process for providing a dental prosthesis, comprising:
    obtaining preoperative digital records and images;
    obtaining a full arch dental restoration design image;
    displaying the full arch dental restoration design image in 3D display format;
    performing steps to create clinical digital records, including:
        attaching at least one from among one or more implants;
        attaching of a multi-unit abutment (MUA) to each of the one or more implants;
        attaching a healing abutment to each MUA; and
        placing of a scan body on each healing abutment, obtaining an intraoral scan (IOS) of the scan body, followed by removal of the scan body, obtaining putty impressions of the healing abutment, and creating the clinical digital records;
    aligning the clinical digital records to the preoperative digital records and images and creating a CAD design of the dental prosthesis;
    manufacturing of the dental prosthesis using the CAD design;
    removing the healing abutments from the MUAs and attaching the dental prosthesis with prosthetic screws to the MUAs and allowing tissue around the dental prosthesis to heal for 3 to 6 months;
    obtaining post-healing digital records by detaching the dental prosthesis from the MUAs, attaching post-healing scan bodies onto the MUAs, placing scannable detection and registration (ScanDAR) material around each post-healing scan body, obtaining a post-healing IOS of the post-healing scan bodies, removing the ScanDAR material and the post-healing scan bodies, placing post-healing healing abutments on each MUA, taking a post-healing putty impression of the post healing abutments and tissue, and obtaining a post-healing IOS to obtain the post-healing digital records;
    aligning the preoperative digital records, the clinical digital records, and the post-healing digital records and forming a final dental restoration design; and
    manufacturing a dental restoration by using the final dental restoration design.

2. The process of claim 1 wherein the final dental prosthesis comprises a full arch dental restoration.

3. The process of claim 1 further comprising using a digital aligner device to obtain the preoperative digital records, the clinical digital records, and the post-healing digital records and forming the final dental restoration design.

4. The process of claim 3 wherein the digital aligner device comprises a fiducial marker that can be utilized two-dimensionally and three-dimensionally to image a human face with multiple facial expressions without changing a position of the human face relative to the fiducial marker.

5. The process of claim 4 wherein the digital aligner device comprises a platform, an alignment plate, and a bent frame that connects the platform to the alignment plate, the bent frame comprising two legs that are bent to a 90 degree or right angle near a top adjacent a connection to the platform, a midline ridge formed on a proximal side wall of the platform to aid in lining up the digital aligner device with a patient's midline, and further comprising one or more openings in the platform to aid in retaining the ScanDAR material on the platform, the alignment plate further including a center section with wings extending from each side, and on an exterior side of the plate are a plurality of alignment domes sized and shaped to allow the digital alignment device to be accurately aligned with other facial scans.

6. The process of claim 4 wherein the digital aligner device is secured to a patient's maxillary teeth or directly to a patient's maxillary edentulous ridge in an event the patient has no remaining maxillary teeth, and remains affixed to the maxillary teeth or maxillary ridge regardless of a facial expression, and wherein during scanning the digital aligner device enables all scans with multiple facial expressions to be aligned with a same exact reference position.

7. The process of claim 1 wherein the MUA comprises an elongated, generally cylindrical body having a substantially planar first end and a truncated conical opposing second end, with a diameter at the first end smaller than a diameter at a beginning of the conical second end, and the first end has two mutually opposing oblique faces formed in a sidewall of the body that extend from the first end onto the body sidewall towards the second end.

8. The process of claim 1 wherein the scan body and the post-healing scan bodies on the post healing abutment each comprise a body having a widening shape from a top to a bottom to enable capturing an entirety of the scan body and the post-healing scan body, the body further including a longitudinal axial bore that extends completely through the body and opens at the top and bottom, the scan body and post-healing scan body each further include coupling geometry that includes one or more encircling or annular geometrical shapes with one or more channels that are designed to capture and secure a settable fluid material, and further comprising longitudinal grooves formed within an exterior surface of the annular geometric shapes that are configured for anti-rotation of the aforementioned material and subsequently the scan body and post-healing scan body themselves within the material, the channels are sized and shaped to allow for and enable dental floss or some other similar material to be wrapped around each scan body and each post-healing scan body individually and enable the dental floss to remain secured while simultaneously wrapping around and adjoining any other of the scan bodies and post-healing scan bodies within an arch.

9. The process of claim 1 wherein the healing abutment and post-healing healing abutment each comprises a main body with a tapered end section having concave side walls, the main body having a truncated conical shape that tapers in diameter from its greatest diameter adjacent the end section to a smallest diameter at a truncated end, the main body further including a single oblique face formed in a circumscribing sidewall of the main body adjacent the truncated end and an annular recess formed inside the main body that opens to the tapered end section, the healing abutment further including a central axial opening that opens into the main body from the truncated end, and further including two shallow openings that are formed in the truncated second end.

10. A process for providing a dental prosthesis, comprising:
    obtaining preoperative digital records and images in a first appointment;
    obtaining a full arch dental restoration design with a customized smile and ideal bite relationship to enable patient visualization in 3D in a first laboratory design;
    performing surgical procedures at a second clinical appointment, including at least one or more of removal of one or more teeth, attachment of one or more implants, attachment of multi-unit abutments (MUAs) to the implants, and attaching of healing abutments to the MUAs, placing of scan bodies on the healing abutments and obtaining an intraoral scan (IOS) of the scan bodies, removing the scan bodies, and obtaining putty impressions of the healing abutments that is then IOS scanned to create digital records;
    aligning the digital records from the second clinical appointment during a second laboratory design to the preoperative digital records and images obtained in the first clinical appointment and designing a dental prosthesis utilizing CAD software, then sending the CAD design to a CAM for manufacturing of the dental prosthesis;
    removing the healing abutments from the MUAs during a third clinical appointment and attaching the dental prosthesis with prosthetic screws to the MUAs and allowing tissue around the dental prosthesis to heal for 3 to 6 months;
    obtaining post-healing digital records in a fourth clinical appointment, detaching the dental prosthesis from the MUAs, attaching post-operative attach scan bodies onto the MUAs, placing scannable detection and registration (ScanDAR) material around each post-operative scan body, obtaining a post operative IOS of the post-operative scan bodies, remove the ScanDAR material and the post-operative scan bodies, placing post-operative healing abutments on each MUA, taking a post-operative putty impression of the post-operative healing abutments and tissue, and obtaining an IOS of the same;
    aligning the digital records in a third laboratory design from all the foregoing steps and forming a final dental restoration design therefrom, and then manufacturing the final dental restoration from the final dental restoration design; and
    removing the post-operative healing abutments from the MUAs in a fifth clinical appointment and attaching the final dental restoration with prosthetic screws to the MUAs.

11. The system of claim 10 wherein the final dental prosthesis comprises a full arch dental restoration.

* * * * *

UNITED STATES PATENT AND TRADEMARK OFFICE
CERTIFICATE OF CORRECTION

| | | |
|---|---|---|
| PATENT NO. | : 11,786,344 B2 | Page 1 of 1 |
| APPLICATION NO. | : 17/532996 | |
| DATED | : October 17, 2023 | |
| INVENTOR(S) | : Jose Arthur Mirelez, Jr. et al. | |

It is certified that error appears in the above-identified patent and that said Letters Patent is hereby corrected as shown below:

In the Claims

<u>Column 13, Claim 1, Lines 65-66:</u>
"the post healing abutments and tissue,"
Should read:
--the post healing healing abutments and tissue,--.

<u>Column 16, Claim 10, Line 15:</u>
"attaching post-operative attach scan bodies"
Should read:
--attaching post-operative scan bodies--.

Signed and Sealed this
Twenty-ninth Day of July, 2025

Coke Morgan Stewart
*Acting Director of the United States Patent and Trademark Office*